(12) United States Patent
Smith, Jr.

(10) Patent No.: US 7,507,214 B2
(45) Date of Patent: Mar. 24, 2009

(54) LUMBAR SELECTIVE STABILIZATION SUPPORT/BRACE

(76) Inventor: Louis Voigt Smith, Jr., 1509 N. 4th St., Tomahawk, WI (US) 54487

(*) Notice: Subject to any disclaimer, the term of this patent is extended or adjusted under 35 U.S.C. 154(b) by 331 days.

(21) Appl. No.: 11/247,472

(22) Filed: Jan. 3, 2006

(65) Prior Publication Data
US 2007/0156073 A1    Jul. 5, 2007

(51) Int. Cl.
*A61F 5/00* (2006.01)
(52) U.S. Cl. ............................................. 602/5; 602/19
(58) Field of Classification Search ...................... 602/5, 602/19; 128/870; 5/644–650
See application file for complete search history.

(56) References Cited
U.S. PATENT DOCUMENTS

| 5,259,831 | A |   | 11/1993 | LeBron |   |
|---|---|---|---|---|---|
| 5,267,948 | A | * | 12/1993 | Elliott | ........................ 602/19 |
| 5,297,304 | A | * | 3/1994 | O'Sullivan | ..................... 5/630 |
| 6,319,217 | B1 |   | 11/2001 | Darcey |   |
| 6,666,838 | B2 |   | 12/2003 | Modglin et al. |   |
| 7,066,181 | B2 | * | 6/2006 | West | ........................ 128/875 |

\* cited by examiner

*Primary Examiner*—Michael A. Brown
(74) *Attorney, Agent, or Firm*—Banner & Witcoff, Ltd.

(57) ABSTRACT

A lumber support device and a selective stabilization support device for use in conjunction with a method of determining and treating mechanical lower back pain such as the McKenzie Approach. The lumber support device includes a semi-rigid member for positioning around the user's abdomen, the member includes a semi-rigid member for positioning around the user's abdomen. The semi-rigid member helps to prevent excessive trunk bending by the patient. At least one tensioning strap is also provided connectable at first and second end regions to a surface of the semi-rigid member. Preferably, two crossed tensioning straps are provided. The straps are provided to encircle the user's torso so as to maintain the lumber support device in position. An adjustable attachment means, for example in the form of a clip, is attached to the straps. The adjustable attachment means is movable laterally along the strap. A pad base is provided on the adjustable attachment means, the pad base being movable with the adjustable attachment means such that its position at the lumber region of the patient can be varied.

19 Claims, 8 Drawing Sheets

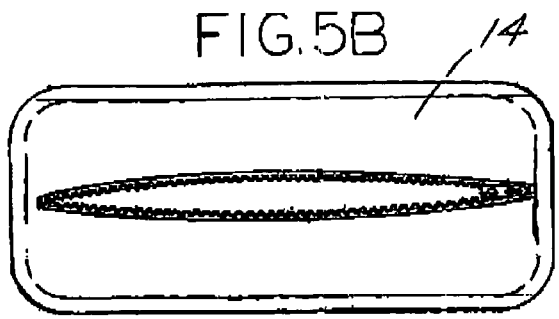
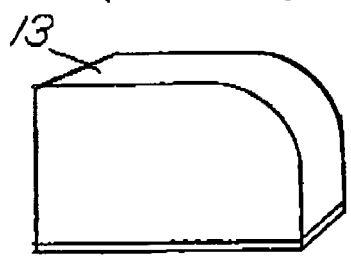
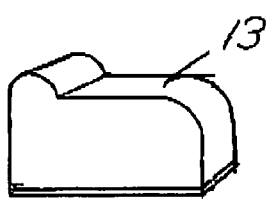
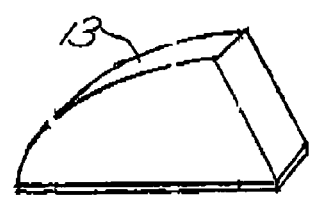
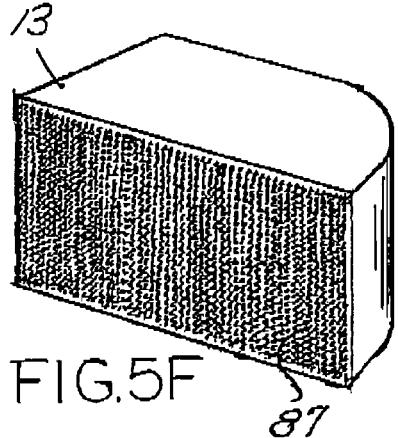
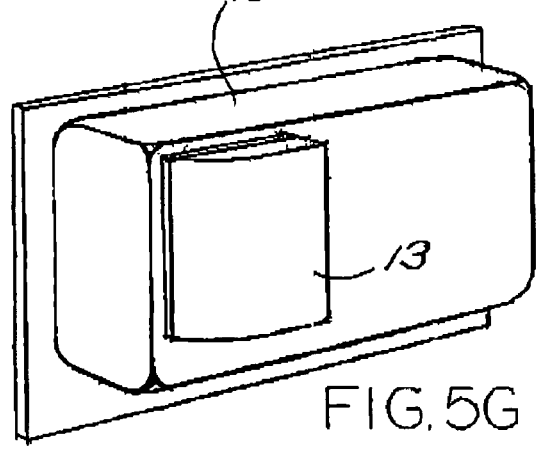

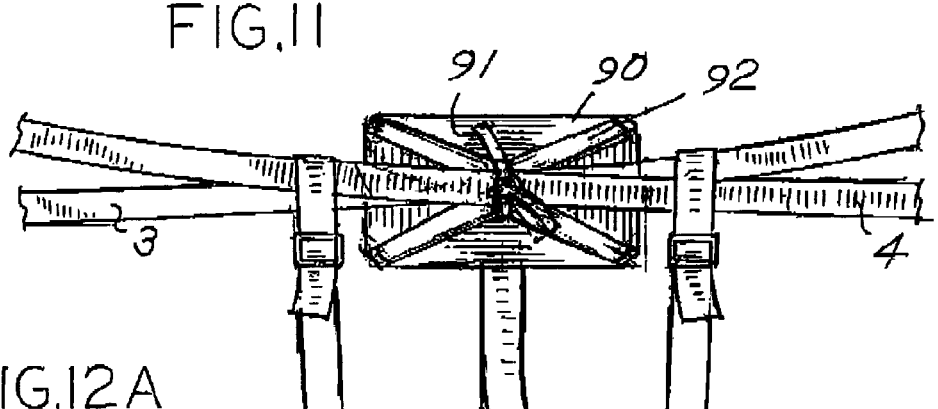
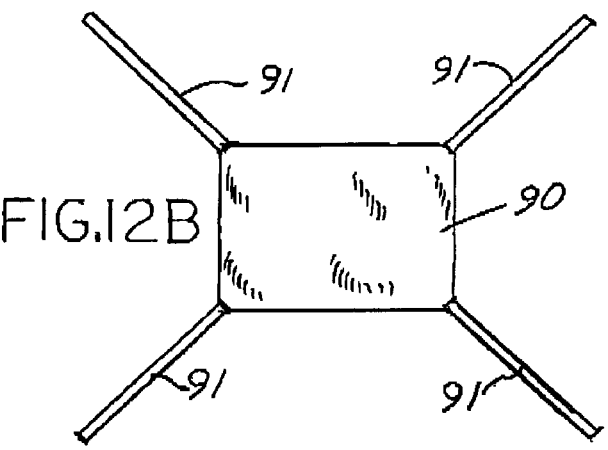
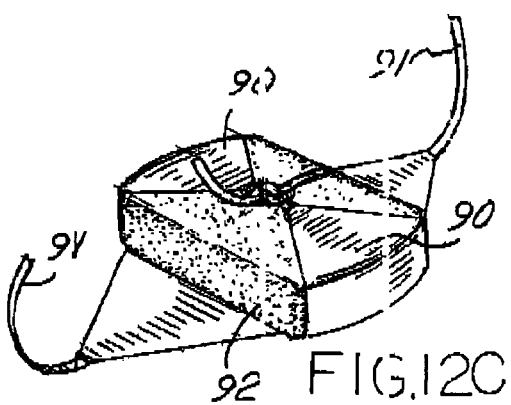
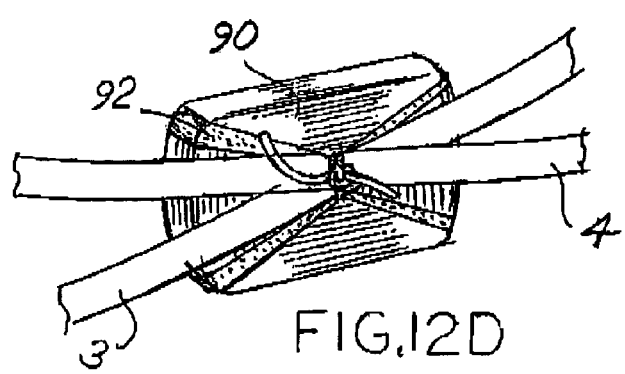

LUMBAR SELECTIVE STABILIZATION SUPPORT/BRACE

BACKGROUND OF THE INVENTION

In a principal aspect the present invention relates to a lumbar support device, a selective stabilization support device and a method of treating mechanical lower back pain using a lumbar support device. In particular, the present invention relates to a versatile lumber support device and a versatile selective stabilization support device for providing selective stabilization of a localized area of a patient's back or neck.

Mechanical back pain is a problem that affects a large proportion of the population at some point in their lives. The pain often occurs as a result of damage to the discs that are provided between the vertebrae in the spine. Damage to these discs can, in turn, result in more pressure being applied to nerve roots, which leads to pain. As people get older, the discs lose hydration and tend to narrow, thus increasing the pressure on the nerve roots. In younger people, the fibers that form the outer walls of the intervertebral discs can become damaged, resulting in fissures in the outer walls of the discs. As the fibers break down, the gel-like substance contained within the disks leaks out, reducing the effectiveness of the discs and increasing the pressure on the surrounding nerves and ligaments. The resulting instability can reduce or block a patient's range of movement and cause pain, weakness and sensory changes. Another cause of back pain is spondylolisthesis, an instability caused by the shifting of one vertebra over another. These types of damage to the spine often occur gradually as a result of poor posture and excessive bending of the back.

At present, mechanical back pain such as that described above is often treated by prescribing drugs to the patient. However, although drugs may reduce the pain experienced by the patient and may reduce the inflammation, they do not address the underlying cause of the pain. Furthermore, surgery is sometimes used to address problems in the spine, for example to remove a damaged segment and to fuse the neighboring vertebrae. Surgery, however, is expensive and invasive, and often does not provide a long lasting solution.

In addition, methods and devices are known for rigidly bracing a patient's back, such as that disclosed in U.S. Pat. No. 5,259,831 for applying rigid thermoplastic panels to the chest and back of a patient to brace the patient's back. The panels provide general support over a large region of the patient's back, but severely restrict the movement of the patient.

Furthermore, devices are also known for providing general support to the lower back region to reduce the likelihood of damage occurring or to treat injury. For example, U.S. Pat. No. 6,319,217 discloses a lumbosacral support pad comprising a moisture-curable resin that hardens upon curing to form a rigid structure that retains its post-curing shape. The support pad is cured in situ on the patient's back such that the resin adopts the contours of the patient's back. Thereafter, the support pad provides general support over the lumber region of the patient's back. In U.S. Pat. No. 6,666,838 there is disclosed a low profile lumbo-sacral orthosis for providing general support to a patient's back to reinforce proper body ergonomics.

These prior art devices are, however, only able to provide general support over the patient's lumbar region. In treating disc derangement, it is desirable to centralize the pain and to therefore reduce the extent of peripheralization, which is the radiation of the pain from a central region to distal regions of the body. For example, back pain may radiate down a patient's legs or other regions.

A known and respected technique for helping to analyze and treat a patient's back pain is the McKenzie Approach. The McKenzie approach involves an organized and systematic mechanical evaluation, categorization and treatment technique for helping to centralize and manage a patient's back pain. According to this approach, the patient's back pain is analyzed by considering the patient's history of back pain, their symptoms, the factors that aggravate or improve the pain and by classifying the pain according to a series of subclassifications. The McKenzie approach can be used, for example, to determine whether a patient has a central lesion of a disc, or a lesion to one side of the disc, and can help categorize mechanical lesions. Furthermore, the McKenzie approach is used to determine the optimum locations, directions and quantities of pressure to apply to selected locations on the patient's back in order to stabilize and centralize the pain.

The patient can then be maneuvered into particular positions by a therapist to help to centralize the pain. This approach is generally successful at helping to reduce a patient's symptoms. However, it is not possible to maintain a patient in these positions such that they are provided with selective stabilization of localized regions of the back for a prolonged period of time. Furthermore, the prior art devices outlined above are not able to provide versatile selective stabilization.

It is therefore desirable to provide support devices that are capable of providing the necessary localized support to selected regions of a patient's back. Furthermore, it is desirable that such support devices be easy to don and doff, comfortable to wear and configurable to different configurations so as to provide the desired support.

SUMMARY OF THE INVENTION

Briefly, the present invention comprises a lumbar support device for providing localized support to a lumbar region of a user comprises: a semi-rigid member for positioning around the user's abdomen, the member being shaped to generally conform with the contours of the user's abdomen; at least one tensioning strap connectable at first and second end regions to attachment means provided on a surface of the semi-rigid member, the at least one tensioning strap being provided to encircle the user's torso so as to maintain the lumbar support device in position; a clip slidably mounted on the at least one tensioning strap, the clip being movable along the at least one tensioning strap; a pad base mounted on the clip, the pad base being movable with the clip along the at least one tensioning strap such that its position at the lumbar region of the user can be varied; and at least one pad mounted on the pad base, the at least one pad being provided to apply pressure to a localized area of the user's lumbar region.

In one embodiment, two tensioning straps are provided, the tensioning straps crossing at the clip. In addition, the clip is preferably a triangular adjustment clip through which the two tensioning straps pass.

In another embodiment, an additional tensioning strap is provided, the additional tensioning strap being connectable at first and second end regions to the surface of the semi-rigid member and being provided with an adjustable attachment means, such as another clip. Another pad base may be mounted on the adjustable attachment means.

In a still further embodiment, the attachment means comprises one or more adhesive strips provided on a front surface of the semi-rigid member, the adhesive strips engaging with material provided at the said first and second end regions of the said at least one tensioning strap.

In addition, the at least one pad is preferably attached to the pad base by means of an adhesive material, such that it is detachable from the pad base. The at least one pad may comprise a compressible material, such as a foam or rubber material. Preferably, the at least one pad is selected from a group of pads having a range of different shapes, sizes and densities. Selection of the at least one pad is made depending upon the location to which it is to be applied and the required pressure to be applied.

Furthermore, the semi-rigid member may comprise a molded base plate having a generally curved shape so as fit comfortably around the user's abdomen.

In a further embodiment, the lumbar support device may further comprise a pair of stabilizing straps, each stabilizing strap being attached at a first end to the pad base or at least one pad and at a second end to the surface of the semi-rigid member. In use, each stabilizing strap passes under the user's crotch. These straps help to maintain the lumbar support device in the desired orientation on the user's body. In particular, they prevent the device from sitting too far (high) up the user's torso.

In a still further embodiment, one or more additional pads may be attached to the at least one tensioning strap at different positions along the strap. Suitable means may be provided on the tensioning strap or straps for attachment of the additional pad or pads. The means may, for example, comprise regions of adhesive material provided on the tensioning strap or straps.

The tensioning strap or straps enable the lumbar support device to be securely fitted around the user's body, such that the device does not slip from its optimal position. Furthermore, adjustment of the straps helps to enable a desired force to be exerted from the pad or pads on the selected localized regions of the patient's back.

According to a second aspect of the invention, there is provided a lumbar support device for providing localized support to a lumbar region of a user, comprising: a semi-rigid member for positioning around the user's abdomen, the member being shaped to generally conform with the contours of the user's abdomen; at least two tensioning straps, the tensioning straps being provided to encircle the user's torso so as to maintain the lumbar support device in position, each said tensioning strap being connectable at first and second end regions to the semi-rigid member, the said tensioning straps being connected by a single, adjustable attachment element to at least one compressible pad, the at least one compressible pad being provided to apply pressure to a localized area of the user's lumbar region.

According to an embodiment of the lumbar support device according to the second aspect of the invention, the said tensioning straps cross over at the said single, adjustable attachment element.

Furthermore, according to a further embodiment of the lumbar support device, the said single, adjustable attachment element comprises a triangular adjustment clip, through which the said tensioning straps pass, and a pad base attached to the triangular adjustment clip and to the at least one pad.

In an alternative embodiment of the lumbar support device, the said single, adjustable attachment element comprises a pad supporting material in which a pad support is wrapped, the pad supporting material being tied around the said tensioning straps such that the pad support can be moved along the tensioning straps to the desired lumber region of the user.

In a still further embodiment of the lumbar support device, the attachment means comprises one or more adhesive strips provided on a front surface of the semi-rigid member, the adhesive strips engaging with material provided at the first and second end regions of the tensioning straps.

In addition, the at least one compressible pad preferably comprises a foam or rubber material.

According to a third aspect of the invention, there is provided a lumbar support device for providing localized support to a lumbar region of a user, comprising: a semi-rigid member for positioning around the user's abdomen, the member being shaped to generally conform with the contours of the user's abdomen; at least two tensioning straps, the tensioning straps being provided to encircle the user's torso so as to maintain the lumbar support device in position, each said tensioning strap being connectable at first and second end regions to the semi-rigid member and each tensioning strap being connected by an adjustable attachment element to a pad support; and at least one pad connected with the pad support, the at least one pad being provided to apply pressure to a localized area of the user's lumber region.

According to an embodiment of the above lumbar support device, the at least two tensioning straps are connected to the same pad support.

According to an alternative embodiment of the above lumbar support device, each of the tensioning straps is connected to a separate pad support.

According to a fourth aspect of the invention, there is provided a selective stabilization support device for providing localized support to a mid-back region of a user, comprising: a base pad for providing localized support to the mid-back region of the user; a holder in which the base pad is contained, the holder being provided with attachment means; two transverse stabilization straps, each connectable at a first end region to the attachment means of the holder and each extending, in use, over a shoulder of the user and substantially vertically down the chest and torso of the user to terminate at a second end region at a leg portion of the user; and two diagonal support straps, each attached at a first end region to the attachment means of the holder and each extending, in use, away from the holder around a side of the user to attach at a second end region to a respective one of the transverse stabilization straps.

According to an embodiment of the selective stabilization support device, a lower neck selective stabilization pad may be attached to one of the transverse stabilization straps or may be provided on a lower neck stabilization strap attached to the holder.

According to another embodiment of the device, a lateral stabilization strap is provided, the lateral stabilization strap being connectable to the attachment means of the holder and extending substantially horizontally around the back and chest of the user in use.

According to another embodiment, the selective stabilization support device further comprises an anterior stabilization strap attached at a first end to one of the transverse stabilization straps and at a second end to the other of the transverse stabilization straps. The anterior stabilization strap may be attached to the transverse stabilization straps by means of an adhesive material.

In a still further embodiment, the second end region of each of the transverse stabilization straps has a clip for attachment to a sock of the user. In addition, one or more leg loop straps may be provided, each being attachable to one of the transverse stabilization straps and, in use, extending around a leg of the user. Furthermore, each transverse stabilization strap may form a loop section around the user's knee, so as not to restrict the user's range of movement.

Preferably, the attachment means provided on the holder comprises regions of adhesive material for attachment to suitable material provided on the straps. In this way, the various straps can be attached and released as desired, enabling different sizes (lengths) of straps to be attached to a particular pad and holder. Alternatively, some or all of the straps may be attached to the pad holder using clips, particularly metal or plastic clips.

Furthermore, the straps are preferably adjustable using adjustment means provided on the straps, such that the lengths of the straps may be adjusted to suit the particular user, and to ensure that the straps are taut in use. Suitable adjustment means may be buckles such as those found on life vests.

According to a fifth aspect of the invention, there is provided a method of applying a lumber support device to treat mechanical lower back pain of a patient, the method comprising: determining that the back pain is mechanical in origin; evaluating the nature and location of the pain; classifying the pain according to a classification system; positioning a semi-rigid member of the lumber support device around the user's abdomen, the member being shaped to generally conform with the contours of the user's abdomen; adjusting at least one tensioning strap connected at first and second end regions to a surface of the semi-rigid member, the at least one tensioning strap encircling the user's torso so as to maintain the lumbar support device in position; selecting a pad having a particular size, shape and density for attachment to the at least one tensioning strap; adjusting the position of the pad relative to the lumbar region of the patient, such that the pad is positioned at a selected localized area of the lumbar region of the patient; and adjusting the tension of the at least one tensioning strap to exert a desired amount of pressure on the localized area using the pad.

According to the fifth embodiment of the invention, a lumbar support device is used in conjunction with the McKenzie approach for determining the nature of mechanical lower back pain to treat the pain. By combining the lumbar support device with such an approach (or other techniques), effective treatment can be provided. Furthermore, a similar method of treatment may be provided by combining the selective stabilization support device with the McKenzie Approach, with physical therapy spinal stabilization exercises or other suitable approaches.

BRIEF DESCRIPTION OF THE DRAWING

In the detailed description which follows, reference will be made to the drawing comprised of the following figures:

FIGS. 5A to 5G show various pad base and pad configurations;

FIG. 11 is a rear view of a lumber support device according to a fourth embodiment of the invention;

FIGS. 12A to 12D show the constitution of an adjustable attachment element of the lumber support device of the fourth embodiment.

DESCRIPTION OF THE PREFERRED EMBODIMENT

Figure 1:
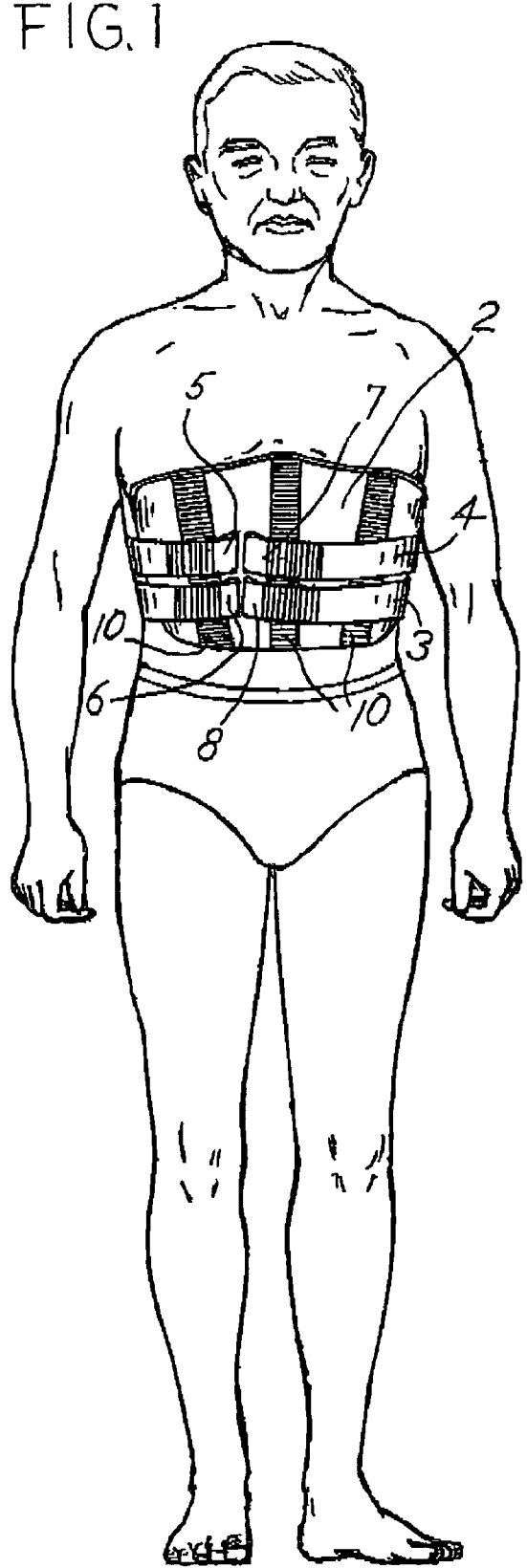
FIG. 1 is a frontal view of a user wearing a lumbar support device according to a first embodiment.
Figure 2:
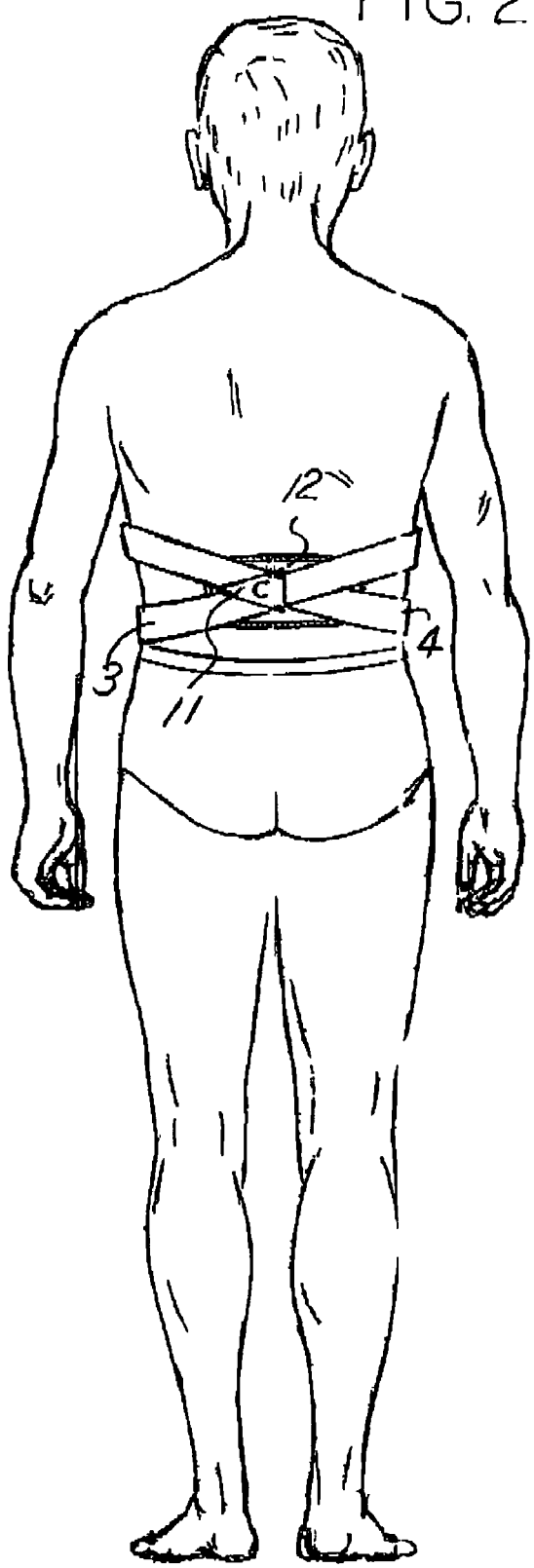
FIG. 2 is a rear view of the user wearing the lumbar support device of the first embodiment.

Referring to the figures, FIGS. 1 and 2 of the accompanying drawings show a lumbar support device according to a first embodiment of the invention. The lumbar support device is used to treat mechanical lower back pain, such as that resulting from disk derangement and spondylolisthesis or other mechanical disorders. In particular, the device provides selective support to a localized area of a patient's lumbar region. Preferably, the device is fitted by a therapist trained in the diagnosis of mechanical lower back pain using the McKenzie approach or any other such technique or approach for diagnosis.

FIG. 1 shows a front view of the device 1 as worn by a user or patient. As can be seen, the device includes a semi-rigid member 2 having a curved shape extending across the abdominal region of the user. Thus, the semi-rigid member is curved so as to generally conform to the contours of the user's abdomen. The semi-rigid member 2 may comprise a molded base plate, such as a molded plastic or thermoplastic plate or panel. Two tensioning straps 3, 4 are provided across the base plate, each tensioning strap being connected at first 5, 6 and second 7, 8 end regions to attachment means 10 located on the front surface of the base plate. The attachment means 10 may comprise regions of adhesive material provided on the front surface of the base plate. More particularly, the attachment means may comprise strips of adhesive material, such as hook and loop fasteners, e.g., Velcro brand fasteners, as shown in the figure.

FIG. 2 shows a rear view of the device 1 worn by the user. It can be seen from this figure that the straps 3, 4 cross over, such that the upper strap 4 on the user's left side becomes the lower strap 4 on the user's right side and the lower strap 3 on the user's left side becomes the upper strap 3 on the user's right side. An adjustable attachment element (means) in the form of a metal adjustor clip 11 is provided at the intersection of the two tensioning straps 3, 4. A pad base 12 is mounted on (attached to) the adjustor clip 11.

Figure 3:
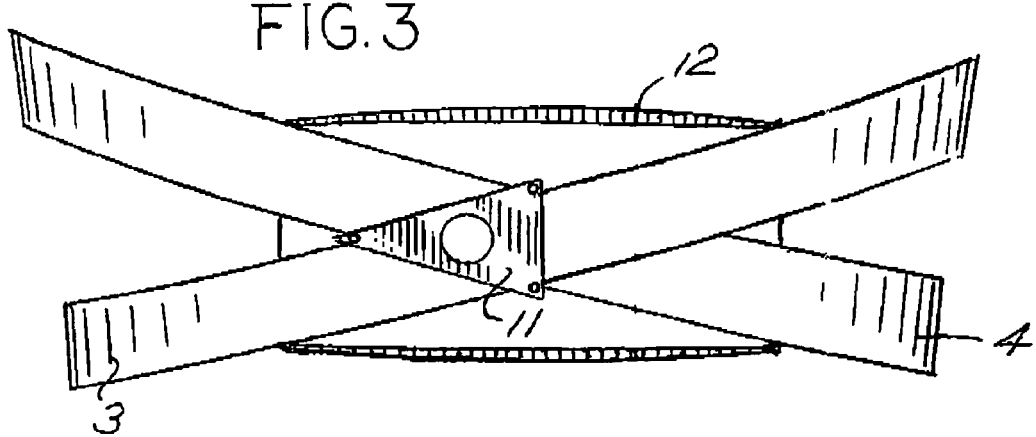
FIG. 3 shows the tensioning straps, clip and pad base of the lumbar support device of the first embodiment.

The metal adjustor clip 11 is formed of two substantially triangular elements connected to one another at the corner regions, with a gap provided between the elements. A plan view of the clip can be seen in FIG. 3. More particularly, the metal adjustor clip is in the form of an isosceles triangle, with each of the tensioning straps passing through the shorter vertical side and one of the other, longer sides of the triangle, such that the straps cross. The pad base 12 is mounted on the clip acting as the adjustable attachment element. Preferably, the pad base 12 is detachable from the clip. For example, the pad base 12 may be attached by means of an adhesive material to the clip 11. Also the clip 11 may be coated or covered with a molded or formed cover (not shown). The cover would then be stabilized from movement (as would clip 11) by hook and loop fasteners attaching the cover to the straps. This would also facilitate the compression in the lumbar region.

Figure 4A:
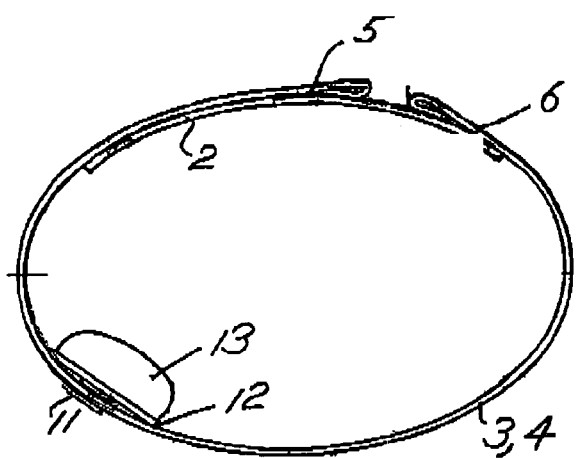
FIGS. 4A to 4C show views of the lumbar support device from above, with the clip and pad base provided at different positions and with different pads attached.
Figure 4B:
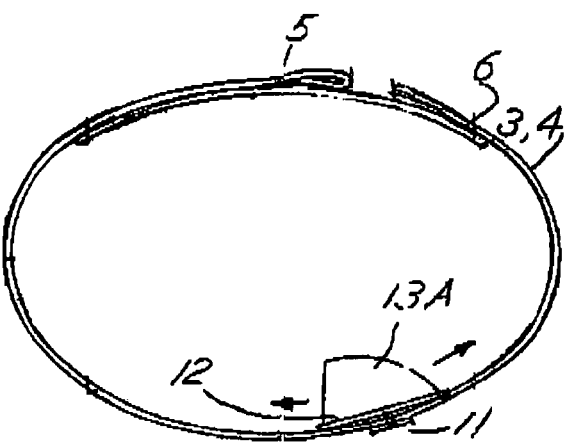
Figure 4C:
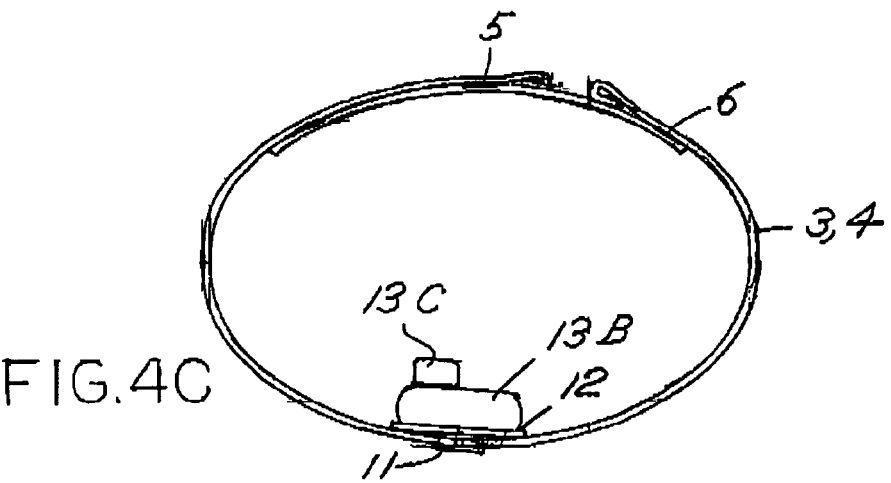

One or more pads 13 can be attached to the pad base, as shown in FIGS. 4A to 4C. The particular number of pads, and the size, shape and density of the pads, can be determined by the therapist fitting the device to the user. In this regard, the therapist may use the McKenzie approach or other such technique for determining the nature of the mechanical lower back pain. Using such a technique, the therapist can determine the localized regions of the user's back to be selectively stabilized using the lumbar support device.

FIG. 4A shows a case where the area to be localized is to the left of the user's spinal column. By sliding the adjustable attachment means (in the form of the clip 11) along the tensioning straps 3, 4, it is possible to vary the position of the pad base 12 in the lumber region of the user. One or more pads 13 can then be attached to the pad base 12. In the example of FIG. 4A, a single pad 13 is used to provide lateral support to a localized region of the user's back. In FIG. 4B, the clip 11 has been moved to the right of the patient's spine, and a pad 13A has been attached to the pad base 12. It can be seen that the pad 13A is different in size and shape to the pad 13. This is because the particular shape, size and density of each of the pads must be carefully chosen by the therapist to best suit the user's (patient's) particular needs; i.e. to position the pad in a therapeutically desirable position. A further example is shown in FIG. 4C, in which two pads 13B and 13C are mounted on the pad base 12. The additional pad 13C provides added support to the desired localized region of the user's back as appropriate, thus enabling satisfactory selective stability to be achieved.

The pads 13 may comprise a compressible material, such as a foam or rubber material. For example, they may comprise EVA compressed foam and/or urethane foam. The different pad sizes, shapes and densities make it possible to customize significant lateral and/or medial support, such as to provide the lateral or medial support required to help centralize ipsilateral back and leg pain. In particular, the different pads allow for selective stabilization at different levels, and make it possible to provide a large quantity of lateral force (providing posterior to anterior medial support) and/or lateral to medial support.

It can also be seen in FIGS. 4A to 4C that the ends of the straps are looped, thus making them easy to grasp and pull for a user.

FIGS. 5A to 5G show different pad configurations. FIG. 5A shows one possible configuration for a base pad, which is the pad mounted on the pad base. The base pad 13D may be provided with regions of adhesive material to adhere it to the pad base 12 and to enable the attachment of additional pads 13 to it. Alternatively, the base pad 13D may be provided inside of a base pad cover 14, the base pad cover being provided with adhesive regions for connection with the pad base 12 and additional pads 13. Such an arrangement is shown in FIG. 5B, where the base pad is zipped inside the base pad cover 14. FIGS. 5C to 5E show possible alternative shapes for the pads (or base pads) 13. Of course, other shapes are possible, and it is not intended to limit the pads to the particular shapes depicted. FIG. 5F shows an additional pad 13 provided with adhesive material on one surface 87 for attachment to a base pad 13D. As can be seen in FIG. 5G, the additional pad may be attached to the base pad by means of the adhesive material. In a similar manner, the base pad may be attached to the pad base 12 using a region of adhesive material provided on the base pad.

The tension in the tensioning straps 3, 4 can be varied by fastening the said first 5, 6 and second 7, 8 end regions to different ones of the vertical strips of adhesive material (constituting the attachment means) provided on the front surface of the semi-rigid member 2. In addition, the angle of pull of the straps can be altered, depending upon the vertical position of attachment to the strips of adhesive material. This in turn helps to ensure that the device is securely and comfortably fitted, and that the required tension is exerted by the pad or pads 13.

Figure 6:
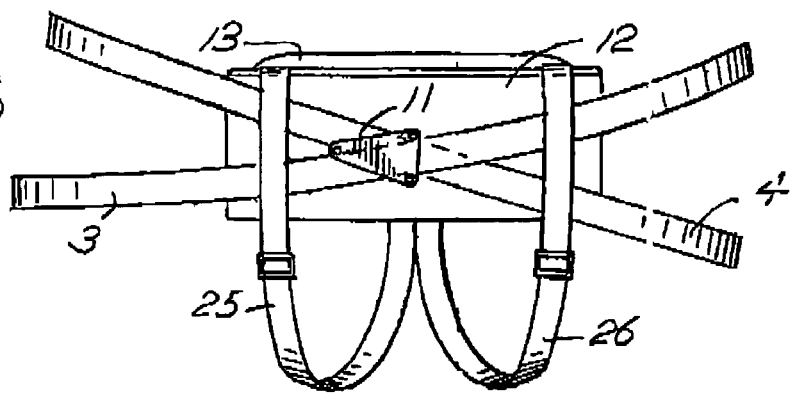
FIG. 6 shows a modification to the lumber support device of the first embodiment to include a pair of stabilizing straps.

As a modification of the lumbar support device according to the above embodiment, a pair of stabilizing straps 25, 26 may be provided additionally. FIG. 6 shows a rear view of the lumbar support device further comprising a pair of such stabilizing straps. Each strap is attached at a first end to a surface of the semi-rigid member 2 and at a second end to either the pad base 12 or a pad 13. In use, each strap loops under the user's groin from the semi-rigid member provided around the user's abdomen to the pad base or pad provided on the user's lower back. These stabilizing straps help to maintain the lumbar support device in position, and to prevent it from twisting, slipping or riding too high up the user's torso. Thus, they help to maintain the pad or pads in the required position, and also help to maintain the overall orientation of the device, ensuring that it is comfortable for the user.

Figure 7:
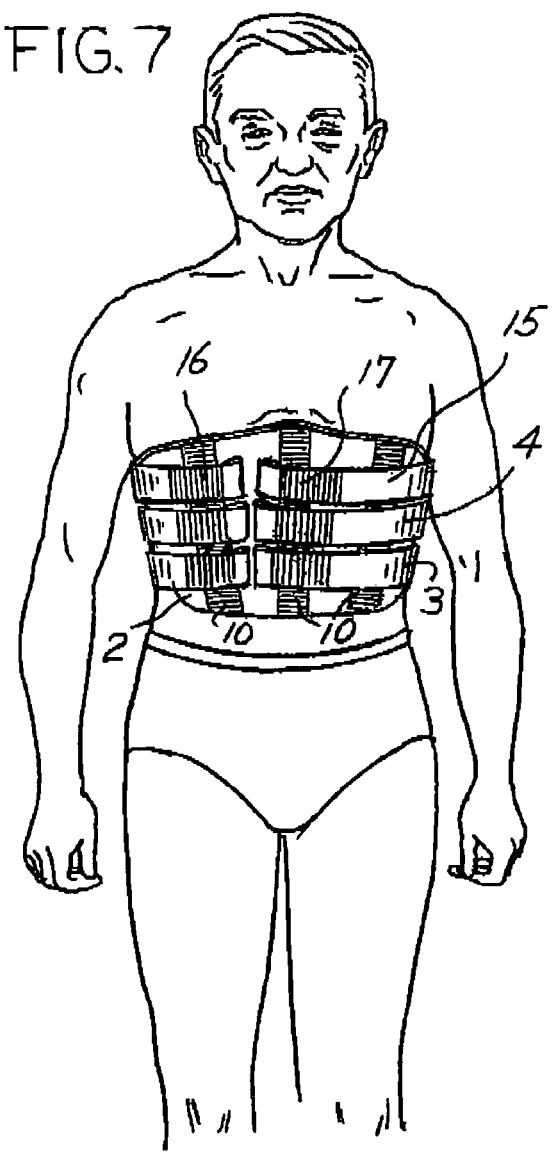
FIG. 7 is a frontal view of a user wearing a lumbar support device according to a second embodiment.
Figure 8:
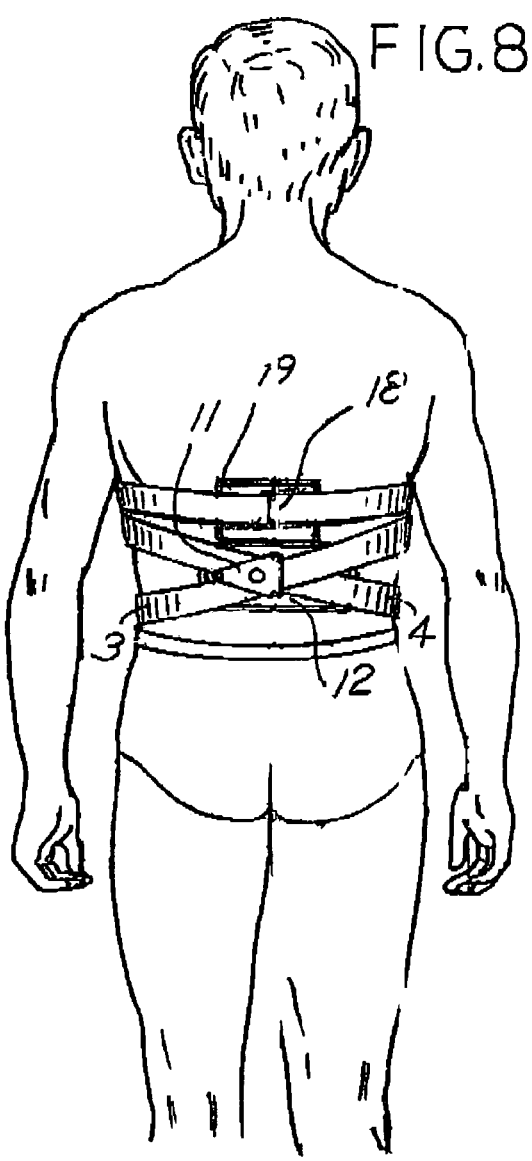
FIG. 8 is a rear view of the user wearing the lumbar support device according to the second embodiment.

FIGS. 7 and 8 show a second embodiment of a lumbar support device according to the invention. According to this embodiment, an additional tensioning strap 15 is provided in addition to the two crossed tensioning straps 3, 4 described above. In other respects, the device is the same as that of the first embodiment. As can be seen from FIG. 7, the additional tensioning strap 15 is connected at first and second end regions 16, 17 to the attachment means 10 provided on the front surface of the semi-rigid member 2. Preferably, the additional tensioning strap can be detached from the semi-rigid member at one or both of its first and second end regions 16, 17. Such a detachable connection may be realized by, for example, providing the attachment means 10 as regions of adhesive material. In particular, as shown in the figure, the attachment means may comprise vertically aligned strips of adhesive material.

FIG. 8 shows a rear view of a user wearing the lumber support device according to this embodiment. The additional tensioning strap 15 is arranged around the user's body above the two crossed tensioning straps 3, 4. A single, adjustable attachment means 18 is provided on the additional tensioning strap. In the figure, a D-ring is depicted as the adjustable attachment means, although any suitable fastening device may be used. Furthermore, an additional pad base 19 may be mounted on the adjustable attachment means 18 and the additional pad base 19 may be connected at a lower side to an upper side of the pad base 12. Alternatively, a single continuous pad base may be provided, comprising the pad bases 12 and 19 and being attached to both the clip 11 of the two crossed tensioning straps and the adjustable attachment means 18 of the additional tensioning strap.

By providing an additional tensioning strap 15 in this manner, it is possible to hold a larger pad base (with a pad or pads mounted thereon) in position at a desired localized region of a user's back. The additional tensioning strap enables the larger pad base to be held tightly against the user's back, to ensure that the desired support is provided to the selected region. Alternatively, the additional tensioning strap 15 enables a second pad base 19 to be provided on the user's back in addition to the first pad base 12. Furthermore, although in the figure the second pad base is shown at a central region of the user's back, immediately above the first pad base, the position of the second pad base 19 may be varied by moving the single, adjustable attachment means 18 laterally along the additional tensioning strap. In this way, localized support can be provided by the lumbar support apparatus to two quite separate regions of the user's back, providing versatile lateral and medial support functions.

Figure 9:
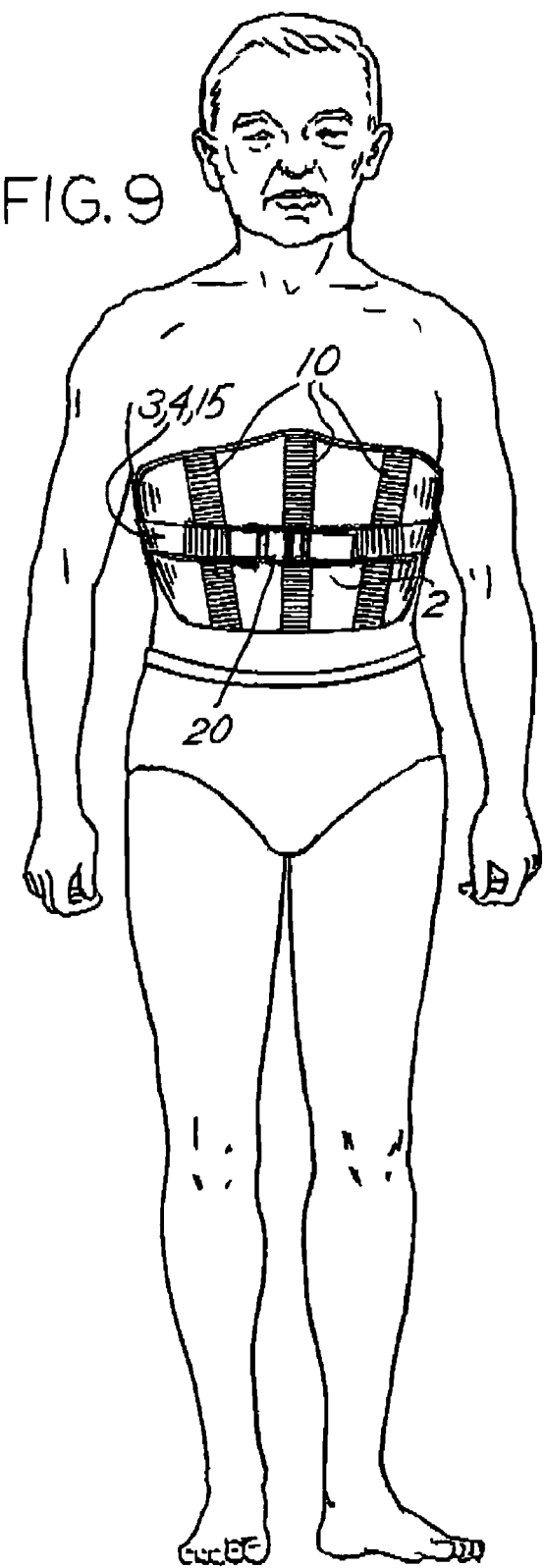
FIG. 9 is a frontal view of a user wearing a lumber support device according to a third embodiment.
Figure 10:
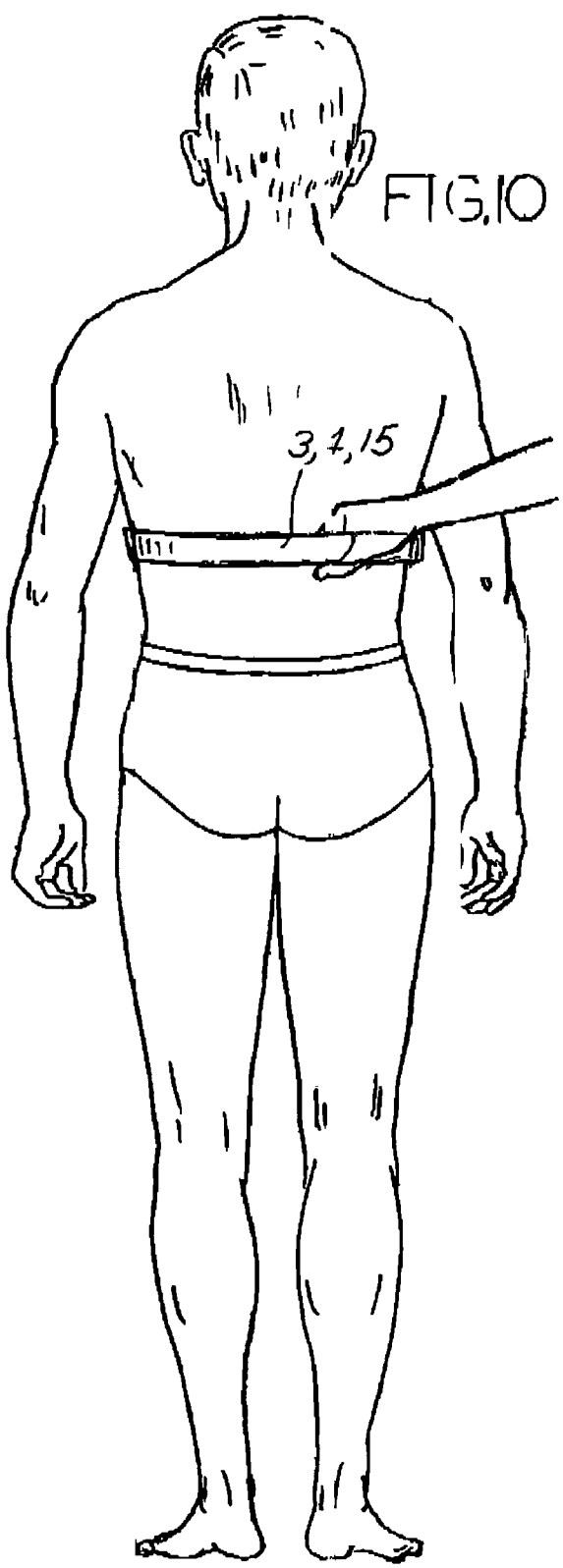
FIG. 10 is a rear view of the user wearing the lumber support device according to the third embodiment.

FIGS. 9 and 10 show a third embodiment of the lumbar support device. Here, a single tensioning strap 3, 4, 15 is shown for simplicity. The strap is provided with adjustment means in the form of a buckle 20 to enable the length of the strap around the user's torso to be varied over a larger range than is otherwise possible. The buckle may, for example, be of the type provided on life vests. By providing adjustment means such as buckles 20 on the straps 3, 4 and 15 of the above described first and second embodiments, it is possible to adjust the tension of the straps more precisely, so as to ensure that the desired tension is achieved and maintained and thus that the required force is applied to the selected localized area or areas of the user's back. Furthermore, by providing crossed tensioning straps 3, 4, selective placement of, and the exertion of strong pressure from, the pads 13 can be reliably and effectively realized.

FIG. 11 shows a rear view of a lumbar support device according to a fourth embodiment of the invention. According to this embodiment, a semi-rigid member and two crossed tensioning straps are provided in a similar manner to the first embodiment described above. In addition, a pair of stabilizing straps is provided in a similar manner to that described with reference to FIG. 6 above. Each of the stabilizing straps is attached at a first end to the semi-rigid member and at a second end to one or both of the two crossed tensioning straps (instead of being attached to a pad base or pad). Furthermore, according to the embodiment of FIG. 11, a pad support 92 is connected to the crossed tensioning straps using an adjustable attachment element, the adjustable attachment element being movable along the crossed tensioning straps, so as to enable the position of the pad support with respect to the user's lumbar region to be varied.

The pad support and adjustable attachment means are shown in more detail in FIGS. 12A to 12D. The pad support is shown in FIG. 12A. As can be seen in FIG. 12B, the adjustable attachment element comprises a pad wrapping material 90 formed by a sheet having strips (ties) 91 provided at its corner regions. The pad wrapping material 90 may comprise a polyester or rubber material. The pad support 92 is wrapped inside of the pad wrapping material and the pad wrapping material is securely fastened around the pad support using two of the strips, as shown in FIG. 12C. The remaining two strips are then used to tie the pad support/pad wrapping material assembly around the two crossed tensioning straps, as can be seen in FIG. 12D. In this manner, the pad support 92 can be securely attached to the tensioning straps and can also be free to move laterally along the straps. One or more additional pads may be attached to the outer surface of the pad wrapping material 90.

In a modification of each of the above described first to fourth embodiments, one or more additional pads may be attached to the tensioning straps at a position or positions different from that of the above described adjustable attachment elements. Such pads may be attached to one of the tensioning straps using an adhesive material, for example. Thus, the lumbar support devices may be configured to best suit a particular patient's needs.

Figure 13:
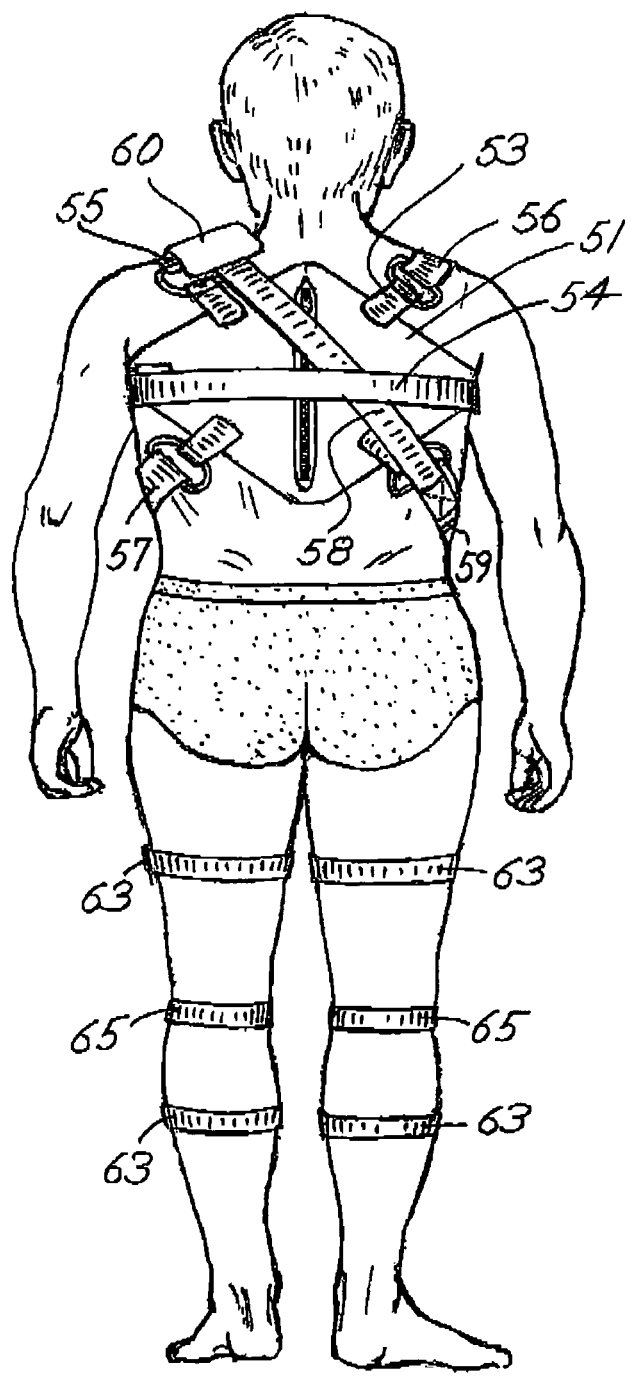
FIG. 13 is a rear view of a user wearing a stabilization support device according to a fifth embodiment of the invention.

FIG. 13 shows a rear view of a user wearing a selective stabilization support device according to a fifth embodiment of the invention. The selective stabilization support device of this embodiment is designed to provide selective support to a mid-back region of a user. Furthermore, the device may be adapted so as to provide selective support to a lower neck region also.

Figure 14:
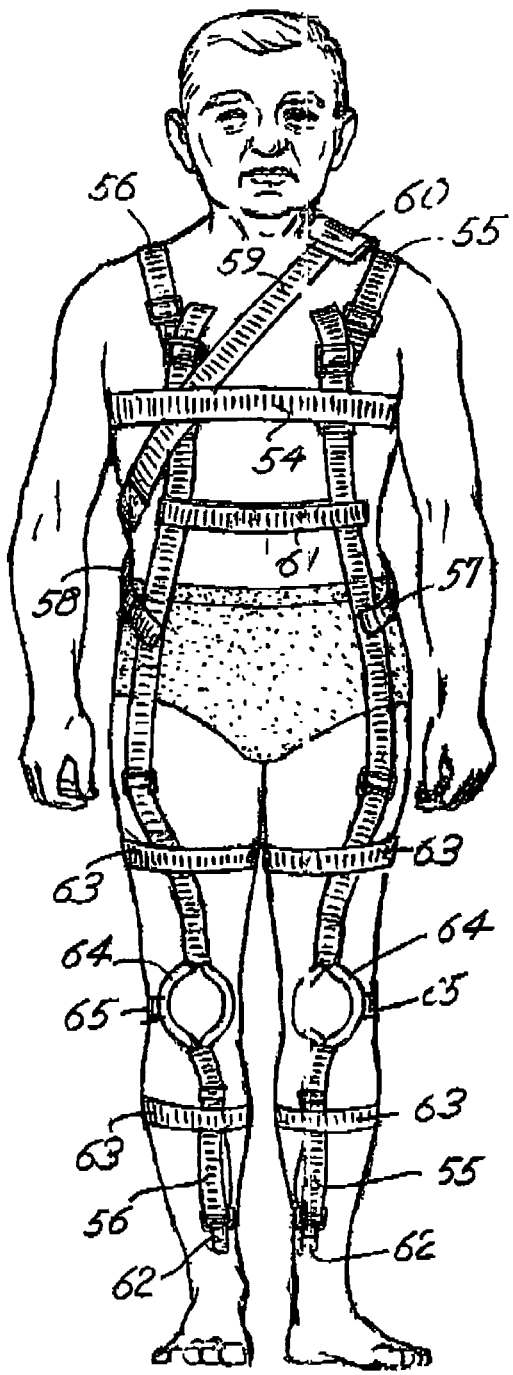
FIG. 14 is a front view of the user wearing the stabilization support device according to the fifth embodiment of the invention.

As can be seen in FIG. 13, the selective support device comprises a pad holder 51 positioned at a mid-back region of the user. A pad 52 is provided inside of the pad holder, the pad being removable from the pad holder. Attachment means 53 may be provided on the holder 51 to enable the attachment and removal of straps to and from the holder, the straps being provided to maintain the pad and holder securely in position. The attachment means may comprise regions of adhesive material. Alternatively, the straps may be provided with clips for attachment to the pad holder. Two transverse stabilization straps 55, 56 are provided, each attachable at a first end region to the holder and each extending, in use, over a shoulder of the user and substantially vertically down the chest and torso of the user to terminate at a second end region at a leg portion of the user, as shown in FIG. 14. Two diagonal support straps 57, 58 are also provided, each attached at a first end region to the holder and each extending, in use, away from the holder around a side of the user to attach at a second end region to a respective one of the transverse stabilization straps. Furthermore, a lateral stabilization strap 54 is provided, the lateral stabilization strap being connectable to the attachment means of the holder and extending substantially horizontally around the back and chest of the user when in use.

In addition, in the embodiment of FIG. 13, a neck stabilization strap 59 is also provided, the neck stabilization strap running diagonally across the user's back and chest and being secured to the holder 51 or other straps by means of regions of adhesive material. A lower neck selective stabilization support pad 60 is mounted on the neck stabilization strap at a lower neck region of the user. The lower neck selective stabilization support pad 60 may be attached to the neck stabilization strap by means of an adhesive material, and is preferably detachable from the strap. Alternatively, the lower neck selective stabilization support pad 60 may be attached to one of the transverse straps 55, 56, as opposed to being provided on its own strap 59. The lower neck selective stabilization support pad enables localized support to be applied to a chosen area of the user's lower neck.

FIG. 14 shows a front view of the user wearing the selective stabilization support device according to the fifth embodiment of the invention. As can be seen in FIG. 14, an anterior stabilization strap 61 may be provided between the transverse stabilization straps. The anterior stabilization strap 61 is positioned across the user's torso below the lateral stabilization strap, and is attached to one of the transverse stabilization straps at a first end and to the other transverse stabilization strap at a second end. It can also be seen in FIG. 14 that clips 62 may be provided at the said second end region of each of the transverse stabilization support straps 55, 56, the clips being for attachment to the socks of the user. In addition, leg loop straps 63 may be provided around the legs of the user, each leg loop strap being attached to one of the said transverse stabilization straps 55, 56, for example by means of a region of adhesive material provided on the leg loop strap and/or on the transverse stabilization strap. Preferably two leg loop straps are provided on each leg of the user, one of the leg loop straps encircling the user's thigh, the other leg loop strap encircling the user's calf. Furthermore, each of the transverse stabilization straps 55, 56 may comprise a central loop strap 64 located at a kneecap region of the user. Each central loop strap forms a loop connected at top and bottom portions to the vertically extending section of its transverse stabilization strap. In addition, a leg loop knee strap 65 may be attached to each of the central loop straps at left and right portions of the central loop strap, the leg loop knee strap extending generally horizontally around the back of the user's knee. By providing straps in this manner around each of the knees of the user, the user's freedom of movement about each knee joint is ensured.

Figure 15:
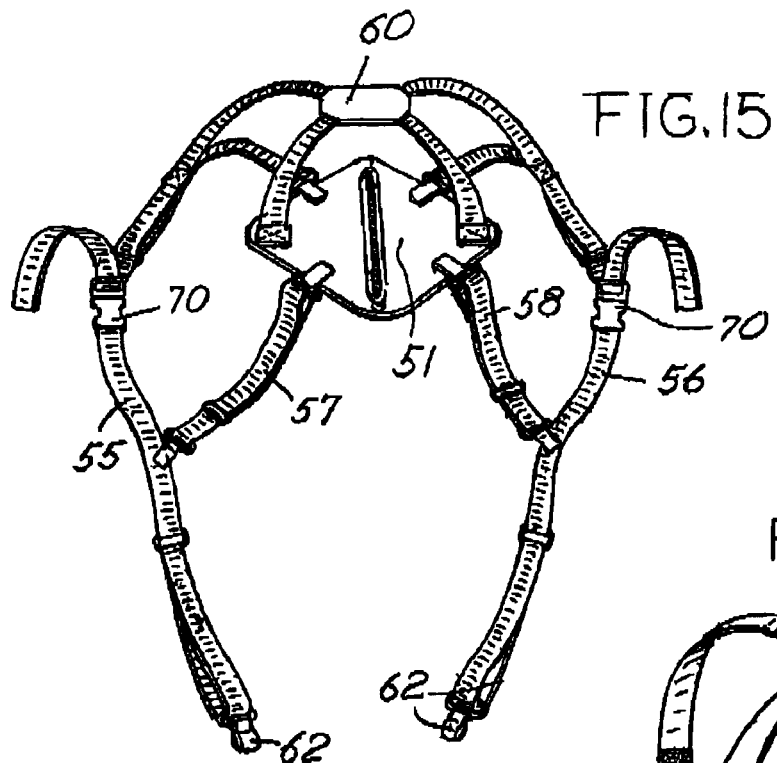
FIG. 15 shows a rear view of a stabilization support device according to a modification of the fifth embodiment of the invention.
Figure 16C:
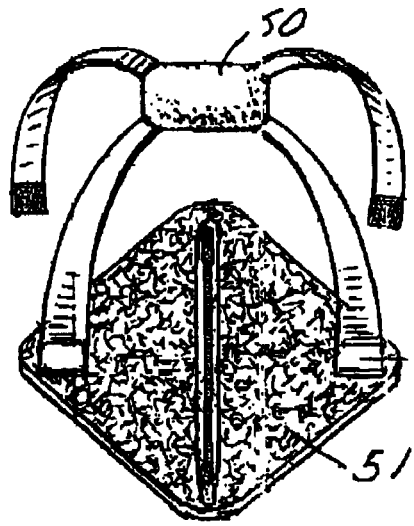
FIGS. 16A to 16C show the configuration of a holder and a support pad of the stabilization support device of FIG. 15.
Figure 16B:
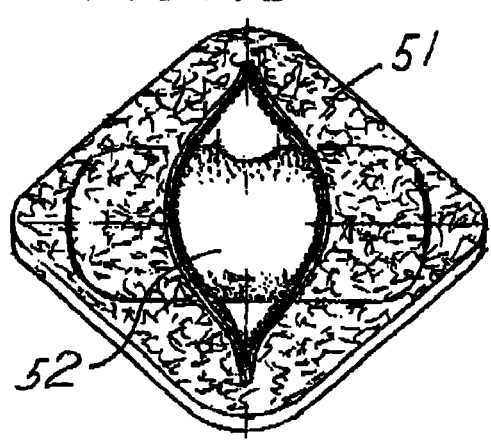
Figure 16A:
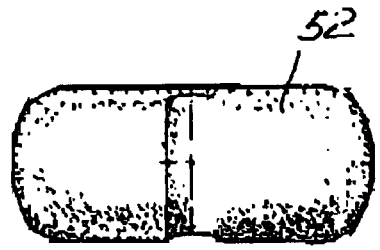

FIG. 15 shows a rear view of a selective stabilization support device according to a modification of this embodiment. In FIG. 15, the transverse stabilization support straps 55, 56 and the diagonal support straps 57, 58 are attached to the holder 51 by means of metal clips. The lower neck selective stabilization pad 60 is provided as a central lower neck pad, and is attached to the holder by means of straps adhered to adhesive regions of the holder. It can also be seen in this figure that adjustment means in the form of buckles 70 are provided on the transverse stabilization straps, to enable the length and tension of those straps to be adjusted. By adjusting the tension of the transverse stabilization straps, the device can be comfortably fitted and secured effectively. Moreover, it can be ensured that the desired force is applied to the mid-back region of the user.

What is claimed is:

1. A lumbar support device for providing adjustable localized support to a lumbar region of a patient, comprising, in combination:
   a semi-rigid member for positioning around an abdomen of a patient, the member being shaped to generally conform with the contours of said abdomen;
   at least two tensioning straps, each strap having first and second end regions, said first and second regions each connectable to the semi-rigid member, at least one of said tensioning straps being provided to encircle the patient's torso so as to maintain the lumbar support device in a prosthetically desirable position; an adjustable, generally triangular clip mechanism slidably mounted on said tensioning straps, said clip mechanism being movable along at least one said tension strap;
   a pad base mounted on the clip mechanism, said pad base being movable with the clip mechanism along said one tensioning strap such that its position at the lumbar region can be varied; and
   at least one pad on the pad base, the at least one pad being provided to apply pressure to said prosthetically desirable localized area of the lumbar region of the patient.

2. The lumbar support device according to claim 1 wherein a further tensioning strap is provided in addition to the said at least one tensioning strap, the further tensioning strap being connectable at first and second end regions to the surface of the semi-rigid member and being provided with an adjustable attachment device.

3. The lumbar support device according to claim 2 including a further pad base mounted on the said adjustable attachment device.

4. The lumbar support device according to claim 3 wherein the said further pad base is connected to the said pad base.

5. The lumbar support device according to claim 1 wherein the attachment means comprises one or more adhesive strips provided on a front surface of the semi-rigid member, the adhesive strips engaging with material provided at the said first and second end regions of the said at least one tensioning strap.

6. The lumbar support device according to claim 1 wherein the at least one pad is detachably mounted on the pad base by means of an adhesive material.

7. The lumbar support device according to claim 1 wherein the at least one pad comprises a compressible material.

8. The lumbar support device according to claim 7 wherein the compressible material is a foam or rubber material.

9. The lumbar support device according to claim 1 wherein the at least one tensioning strap is adjustable to vary the applied pressure.

10. The lumbar support device according to claim 1 wherein the semi-rigid member comprises a molded base plate.

11. The lumbar support device according to claim 1 further comprising a pair of stabilizing straps, each stabilizing strap being attached at a first end to the said pad base or said at least one pad and at a second end to the said surface of the semi-rigid member, so as to loop around the user's groin in use.

12. The lumber support device according to claim 1 further comprising an additional pad attached to the at least one tensioning strap at a position different to that of the said clip mechanism.

13. A lumbar support device for providing localized support to a lumbar region of a patient, comprising, in combination:
   a semi-rigid member for positioning around an abdomen or said patient, the member being shaped to generally conform with the contours of the abdomen;
   at least two tensioning straps, the tensioning straps being provided to encircle the patient's torso so as to maintain the lumbar support device in position, each said tensioning strap being connectable at first and second end regions to the semi-rigid member, the said tensioning straps being connected by a single, adjustable attachment element to at least one compressible pad, the at least one compressible pad being provided to apply pressure to a localized area of the user's lumbar region of the patient;
   said single, adjustable attachment element comprising a generally triangular adjustment clip, through which the said tensioning straps pass; and
   a pad base attached to the triangular adjustment clip and to the at least one pad.

14. The lumbar support device according to claim 13 wherein the said tensioning straps cross over at the said single, adjustable attachment element.

15. The lumbar support device according to claim 13 wherein the said single, adjustable attachment element comprises a pad supporting material in which a pad support is wrapped, the pad supporting material being tied around the said tensioning straps such that the pad support can be moved along the tensioning straps to the desired lumber region of the user.

16. The lumbar support device according to claim 13 wherein the attachment means comprises one or more adhesive strips provided on a front surface of the semi-rigid member, the adhesive strips engaging with material provided at the first and second end regions of the tensioning straps.

17. The lumbar support device according the claim 13 wherein at least one compressible pad comprises a foam or rubber material.

18. A lumbar support device for providing localized support to a lumbar region of a patient, comprising, in combination:
   a semi-rigid member for positioning around the abdomen of a patient, the member being shaped to generally conform with the contours of the user's abdomen;

at least two tensioning straps, the tensioning straps being provided to encircle the torso of said patient so as to maintain the lumbar support device in position, each said tensioning strap being connectable at first and second end regions to the semi-rigid member and said tensioning straps being crossed and connected by an adjustable attachment element to a pad support, said adjustable attachment element comprising first and second elements having a gap therebetween for slidable and adjustable receipt of said crossed tensioning straps with the pad support mounted on said attachment element; and at least one pad connected with the pad support, the at least one pad being postionable to apply pressure to a localized area of the lumber region of said patient by slidable movement of the attachment element along at least one said tensioning strap.

19. The lumbar support device of claim 18 further including a second pad support device slidably mounted on at least one of said tensioning straps.

* * * * *